(12) United States Patent
Winter et al.

(10) Patent No.: US 11,013,457 B2
(45) Date of Patent: May 25, 2021

(54) METHOD AND DEVICE FOR TREATING ATAXIC BREATHING (71) Applicant: KONINKLIJKE PHILIPS N.V., Eindhoven (NL)

(72) Inventors: Stefan Winter, Würselen (DE); Eugene Nelson Scarberry, Trafford, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 288 days.

(21) Appl. No.: 15/779,906

(22) PCT Filed: Nov. 21, 2016

(86) PCT No.: PCT/EP2016/078220
§ 371 (c)(1),
(2) Date: May 30, 2018

(87) PCT Pub. No.: WO2017/093054
PCT Pub. Date: Jun. 8, 2017

(65) Prior Publication Data
US 2018/0368758 A1    Dec. 27, 2018

Related U.S. Application Data

(60) Provisional application No. 62/261,359, filed on Dec. 1, 2015.

(30) Foreign Application Priority Data

Jan. 6, 2016 (EP) ..................................... 16150293

(51) Int. Cl.
*A61B 5/00* (2006.01)
*A61B 5/08* (2006.01)
(Continued)

(52) U.S. Cl.
CPC .......... *A61B 5/4818* (2013.01); *A61B 5/0205* (2013.01); *A61B 5/087* (2013.01);
(Continued)

(58) Field of Classification Search
CPC .......... A61M 16/0045; A61M 16/0048; A61M 16/0051; A61M 16/0054; A61M 16/0057;
(Continued)

(56) References Cited

U.S. PATENT DOCUMENTS 4,537,190 A    8/1985  Caillot
5,107,830 A *  4/1992  Younes ................. A61M 16/00
                                          128/204.18

(Continued)

FOREIGN PATENT DOCUMENTS

EP    324275 A1    7/1989
EP    1350466 A1   10/2003
(Continued)

OTHER PUBLICATIONS

Ramar, K. et al., "Adaptive Servoventilation in Patients with Central or Complex Sleep Apnea Related to Chronic Opioid Use and Congestive Heart Failure", Journal of Clinical Sleep Medicine, vol. 8, No. 5, 2012.

*Primary Examiner* — Justine R Yu
*Assistant Examiner* — Kelsey E Baller (57) ABSTRACT

The present invention relates to a method for re-synchronizing a breathing pattern of a patient (16) suffering from ataxic breathing, the method including the steps of monitoring the breathing pattern of the patient (16) during sleep; detecting whether the monitored breathing pattern includes an ataxic breathing episode; and if an ataxic breathing episode is detected, ventilating the patient (16) and eliminating a spontaneous breathing of the patient (16) for a predetermined first period of time ($\Delta t_1$) by providing a flow (Continued)

of breathing gas (14) to an airway of the patient (16) with a volume of the breathing gas (14) provided per minute being above an individual-related threshold value of the patient (16).

14 Claims, 3 Drawing Sheets

(51) Int. Cl.
| | |
|---|---|
| *A61B 5/087* | (2006.01) |
| *A61B 5/113* | (2006.01) |
| *A61B 16/00* | (2006.01) |
| *A61B 5/0205* | (2006.01) |
| *A61M 16/00* | (2006.01) |

(52) U.S. Cl.
CPC ............ *A61B 5/0816* (2013.01); *A61B 5/113* (2013.01); *A61B 5/1135* (2013.01); *A61B 5/4076* (2013.01); *A61B 5/4806* (2013.01); *A61B 5/7282* (2013.01); *A61M 16/0051* (2013.01); *A61M 16/024* (2017.08); *A61B 5/082* (2013.01); *A61B 5/725* (2013.01); *A61B 2562/0219* (2013.01); *A61B 2562/0247* (2013.01); *A61M 2205/0294* (2013.01); *A61M 2205/332* (2013.01); *A61M 2205/3334* (2013.01); *A61M 2205/50* (2013.01); *A61M 2230/005* (2013.01); *A61M 2230/42* (2013.01)

(58) Field of Classification Search
CPC ............ A61M 16/006; A61M 16/0063; A61M 16/0066; A61M 16/0069; A61M 16/0072; A61M 16/0075; A61M 16/0078; A61M 16/0081; A61M 16/0084; A61M 16/0087; A61M 16/009; A61M 16/0096; A61M 16/0093; A61M 16/01–026; A61M 16/00; A61M 16/0003; A61M 16/0006; A61M 16/0009; A61M 16/0012; A61M 16/024; A61B 5/4818; A61B 5/0816; A61B 5/0826; A61B 5/087; A61B 5/113; A61B 5/1135; A61B 5/4076; A61B 5/4806; A61B 5/7282; A61H 2016/0015; A61H 2016/0018; A61H 2016/0021; A61H 2016/0024; A61H 2016/0027; A61H 2016/003; A61H 2016/0033; A61H 2016/0036; A61H 2016/0039; A61H 2016/0042

USPC .................................................. 128/204.23
See application file for complete search history.

(56) References Cited

U.S. PATENT DOCUMENTS

| | | | |
|---|---|---|---|
| 5,245,995 A | 9/1993 | Sullivan et al. | |
| 5,645,054 A | 7/1997 | Cotner et al. | |
| 5,937,853 A | 8/1999 | Strom | |
| 6,126,611 A * | 10/2000 | Bourgeois | A61N 1/3601 600/508 |
| 7,077,810 B2 * | 7/2006 | Lange | A61B 5/0823 600/538 |
| 7,810,497 B2 | 10/2010 | Pittman | |
| 8,261,742 B2 | 9/2012 | Strothmann et al. | |
| 8,701,665 B2 * | 4/2014 | Tehrani | A61M 16/024 128/204.23 |
| 9,044,560 B2 | 6/2015 | Shelly et al. | |
| 2002/0015034 A1 * | 2/2002 | Malmborg | G06F 3/033 345/204 |
| 2002/0185127 A1 | 12/2002 | Melker | |
| 2005/0061315 A1 | 3/2005 | Lee et al. | |
| 2006/0070624 A1 | 4/2006 | Kane | |
| 2006/0279428 A1 * | 12/2006 | Sato | A61B 5/0064 340/575 |
| 2008/0092894 A1 * | 4/2008 | Nicolazzi | A61M 16/0051 128/204.23 |
| 2011/0112442 A1 * | 5/2011 | Meger | A61B 5/4094 600/595 |
| 2011/0288609 A1 | 11/2011 | Tehrani et al. | |
| 2011/0297156 A1 | 12/2011 | Shelly | |
| 2012/0179061 A1 * | 7/2012 | Ramanan | A61B 5/4812 600/538 |
| 2013/0152934 A1 * | 6/2013 | Mulqueeny | A61M 16/0069 128/204.23 |
| 2013/0197321 A1 | 8/2013 | Wilson | |
| 2014/0123979 A1 | 5/2014 | Doyle et al. | |
| 2014/0202455 A1 * | 7/2014 | Garde | A61B 5/4836 128/200.14 |
| 2014/0323874 A1 * | 10/2014 | Addison | A61B 5/14552 600/473 |
| 2016/0151594 A1 * | 6/2016 | Truschel | A61M 16/024 128/204.23 |
| 2018/0104426 A1 * | 4/2018 | Oldfield | A61B 5/091 |

FOREIGN PATENT DOCUMENTS

| | | |
|---|---|---|
| EP | 1410755 A1 | 4/2004 |
| GB | 2472116 A | 1/2011 |
| JP | H0819610 A | 1/1996 |
| JP | 2014147595 A | 8/2014 |
| WO | 2009138976 A2 | 11/2009 |

* cited by examiner

METHOD AND DEVICE FOR TREATING ATAXIC BREATHING

CROSS-REFERENCE TO PRIOR APPLICATIONS

This application is the U.S. National Phase application under 35 U.S.C. § 371 of International Application Serial No. PCT/EP2016/078220, filed on 21 Nov. 2016, which claims the benefit of U.S. Application Ser. No. 62/261,359, filed on 1 Dec. 2015 and European Application Serial No. 16150293.5, filed on 6 Jan. 2016. These applications are hereby incorporated by reference herein.

FIELD OF THE INVENTION

The present invention relates to a method for re-synchronizing a breathing pattern of a patient suffering from ataxic breathing. The present invention furthermore relates to a corresponding device for re-synchronizing a breathing pattern of a patient suffering from ataxic breathing. Still further, the present invention relates to a corresponding computer program.

BACKGROUND OF THE INVENTION

In recent years the number of patients suffering from ataxic breathing is increasing more and more. Ataxic breathing is an abnormal pattern of breathing characterized by a complete irregularity of breathing. This phenomenon typically only occurs while the patients are sleeping. Patients suffering from ataxic breathing have a very irregular breathing pattern during sleep affecting both frequency and amplitude of breaths.

It is caused by damage to the medulla oblongata. Neurological changes affect the control loop responsible for breathing and in this way lead to the occurrence of ataxic breathing episodes during sleep. Ataxic breathing is often observed in patients using opiods and has negative effects comparable to those of regular sleep apnea. Due to the comparatively frequent administration of opioids in the US, ataxic breathing has become a more and more frequently observed problem especially (but not only) in the US.

Due to its irregularity it is difficult to predict the amplitude and timing of the next breath and correspondingly the optimal way of treating ataxic breathing. The most common way of treating ataxic breathing is by means of a positive airway pressure (PAP) therapy. While existing PAP therapy modes are quite suitable for treating "regular" sleep apnea, these existing PAP therapy modes are, however, not optimal for the treatment of ataxic breathing.

GB 2 472 116 discloses a method and an apparatus for controlling a ventilator to automatically adjust ventilation assistance to an active or passive subject.

US 2014/0123979 discloses systems and methods for determining patient fatigue during ventilation of a patient.

EP 0 324 275 discloses a ventilation synchronizer.

US 2005/0061315 discloses methods and systems which involve monitoring one or more patient conditions using a monitoring device that is fully or partially implantable.

US 2011/0288609 discloses a method and device for treating a variety of conditions, disorders or diseases with diaphragm/phrenic nerve stimulation.

EP 1 350 466 discloses a monitor which can detect respiration of a sleeping person without being affected by the attitude of the sleeping person or the indoor illumination light and which can easily evaluate detected respiration quantitatively through image measurement.

EP 1 410 755 discloses a monitoring device which can detect conditions of a sleeping person.

WO 2009/138976 discloses monitoring, predicting and treating clinical episodes. A control unit is configured to monitor a condition of the subject by analyzing a physiological parameter and sensed body movement for driving an output unit to generate an alert upon detecting a deterioration of the monitored condition.

There is therefore still room for improvement.

SUMMARY OF THE INVENTION

It is an object of the present invention to provide an improved method and device for treating ataxic breathing.

In a first aspect of the present invention a method for re-synchronizing a breathing pattern of a patient suffering from ataxic breathing is presented, wherein the method includes the steps of:
  monitoring the breathing pattern of the patient during sleep;
  detecting whether the monitored breathing pattern includes an ataxic breathing episode; and
  if an ataxic breathing episode is detected, ventilating the patient and eliminating a spontaneous breathing of the patient for a predetermined first period of time by providing a flow of breathing gas to an airway of the patient with a volume of the breathing gas provided per minute being above an individual-related threshold value of the patient.

In a further aspect of the present invention a corresponding device is presented which comprises:
  a sensor for monitoring the breathing pattern of the patient during sleep, wherein the sensor generates a breathing signal;
  a pressure generator for generating a flow of breathing gas;
  a pressure circuit including a patient interface for guiding the generated flow of breathing gas to an airway of the patient; and
  a controller which is configured to:
    evaluate the breathing signal in order to detect whether the monitored breathing pattern includes an ataxic breathing episode; and
    if an ataxic breathing episode is detected in the breathing signal, control the pressure generator to provide for a predetermined first period of time the flow of breathing gas with a volume per minute being above an individual-related threshold value of the patient so as to ventilate the patient and eliminate a spontaneous breathing of the patient for said predetermined first period of time.

In a still further aspect of the present invention a computer program is presented which comprises program code means for causing a computer to carry out the steps of the above-mentioned method when said computer is carried out on a computer.

Preferred embodiments of the invention are defined in the dependent claims. It shall be understood that the claimed device and the claimed computer program have similar and/or identical preferred embodiments as the claimed method and as defined in the dependent claims.

The proposed method and device make use of a positive airway pressure treatment which causes a re-synchronization of the breathing of the patient as soon as an ataxic breathing episode is detected. As long as the patient's breathing pattern is within predetermined boundaries and no ataxic breathing episode is detected, preferably no pressure support is applied, i.e. no pressurized flow of breathing gas is supplied to the airway of the patient. However, if the breathing pattern shows signs of ataxic breathing, the generation and delivery of the pressurized flow of breathable gas is initiated. The flow of breathable gas is in this case delivered to the airway of the patient with a volume provided per minute that is above an individual-related threshold value of the patient. This individual-related threshold value of the patient is the amount/volume of breathing gas that the person usually requires during normal breathing. The individual-related threshold value preferably equals the minute ventilation during normal breathing, i.e. during phases in which no ataxic breathing episodes are occurring and the person is at rest or sleeping.

Minute ventilation is defined as the volume of gas inhaled or exhaled from a person's lung per minute. It is an important parameter in respiratory medicine due to its relationship with blood carbon dioxide levels. However, it shall be noted that the minute ventilation during regular breathing differs from patient to patient and depends on several anatomical factors, such as height, weight, etc. The threshold value of the volume of the provided breathing gas per minute that is according to the presented method and device exceeded is thus also an individual-related value that may differ from patient to patient.

Since the afore-mentioned individual-related threshold value, which is indicative of the minute ventilation of the patient during normal breathing, is exceeded, the patient's spontaneous breathing is eliminated during the provision of the pressurized flow of breathable gas. To this end, the patient's breathing is so to say overdriven by means of the externally provided mechanical ventilation. The spontaneous breathing efforts are overruled.

Supplying a person who is suffering from an irregular breathing pattern with a flow of breathing gas having a volume flow per minute that is well in excess of what the person would need during normal breathing will override the person's irregular breathing pattern and return him/her to more normal breathing. One mechanism behind this effect is that the irregular breathing pattern will throw the normal exchange of $O_2$ and $CO_2$ off balance. Providing the afore-mentioned flow of pressurized breathing gas will help restoring the balance of $O_2$ and $CO_2$ to more normal values, which increases the chances of the person being able to start following a more normal spontaneous breathing pattern again.

In other words, the chemosensors, which are usually not working in a right manner when ataxic breathing is occurring, shall be overruled and the brain shall be stopped from causing neurological signals that lead to the ataxic breathing episodes. Since the spontaneous breathing is eliminated due to the applied breathing gas above the "normally" needed minute ventilation threshold, the breathing pattern is re-synchronized in a similar way as the hearth rhythm is re-synchronized by an implantable cardioverter defibrillator (ICD).

It is important to note that the patient is within the herein presented method ventilated in a way that eliminates the spontaneous breathing of the patient. This has to be clearly distinguished from PAP treatments such as CPAP or Bi-PAP treatments that are used for treating "regular" sleep apnea diseases. CPAP and Bi-PAP therapy modes make use of lower volume flows, since these therapy modes are intended for preserving the patency of the patient's airway, i.e. for keeping the patient's airway open, but not for mechanically ventilating the patient. CPAP and Bi-PAP therapy modes still allow the patients to breathe spontaneously. In contrast thereto, such a spontaneous breathing is not possible during the provision of the flow of breathing gas in the treatment according to the present invention.

According to an embodiment of the presented method, the step of detecting an ataxic breathing episode includes evaluating one or more of a minute ventilation, a breathing frequency, and a breathing amplitude of the patient, wherein a part of the monitored breathing pattern of the patient is identified as ataxic breathing episode if a variation over time of the one or more of the minute ventilation, the breathing frequency, and the breathing amplitude of the patient is larger than a predetermined threshold.

According to a corresponding embodiment of the presented device, the controller is configured to:
  determine one or more of a minute ventilation, a breathing frequency, and a breathing amplitude of the patient based on the breathing signal;
  evaluate a variation over time of the one or more of the minute ventilation, the breathing frequency, and the breathing amplitude; and
  identify a part of the monitored breathing pattern of the patient as ataxic breathing episode if the variation over time of the one or more of the minute ventilation, the breathing frequency, and the breathing amplitude of the patient is larger than a predetermined threshold.

Large variations in frequency and/or amplitude which also lead to variations of minute ventilation are usually good indicators for detecting ataxic breathing. The breathing pattern of the patient may be monitored by a sensor, wherein several types of different sensors are generally conceivable to be used.

According to an embodiment of the presented device, the sensor may include at least one of a flow sensor, a pressure sensor, a camera, a radar sensor, an accelerometer, a piezoelectric sensor and an electrochemical gas sensor.

A flow sensor may e.g. be arranged within the pressure circuit at or close to the patient interface via which the flow of breathing gas is delivered to the airway of the patient.

A pressure sensor may be arranged at the same location, either alternatively to the flow sensor or in addition thereto.

Another way of monitoring the breathing pattern of the patient is by means of a camera. With today's cameras, such as e.g. the Philips Vital Signs Camera, it is no problem to derive a breathing pattern from an optical camera signal.

It would be similarly possible to derive the breathing pattern by means of a radar sensor.

Still alternatively, an accelerometer or piezoelectric sensor could be used for this task, wherein the accelerometer or the piezoelectric sensor is e.g. arranged at the chest of the patient.

A still further possibility is the usage of an electrochemical gas sensor that is configured to measure the composition of the breathing gas that is exhaled by the patient. This electrochemical gas sensor may also be arranged within the pressure circuit, e.g. at or within the patient interface.

It shall be noted that independent of the type of sensor that is used, the signal generated by this sensor is herein denoted as breathing signal, as this signal is indicative of the person's breathing pattern. As a consequence, this breathing signal may either be a flow signal, a pressure signal, an optical signal, etc.

The generated flow of breathing gas that is according to the present invention used in the above-mentioned way for re-synchronizing the breathing pattern of the patient is preferably provided only for a comparatively short time period each time an ataxic breathing episode is detected. This time period is herein denoted as first period of time or first time period. This predetermined first period of time is preferably set to be shorter than ten minutes, more preferably shorter than five minutes, most preferably shorter or equal to three minutes.

In a preferred embodiment of the presented method, the method comprises the steps of:
(i) discontinuing the provision of the breathing gas after the predetermined period of time for at least a second predetermined period of time;
(ii) monitoring the breathing pattern of the patient during the second predetermined period of time;
(iii) if an ataxic breathing episode is detected during the second period of time, ventilating the patient and eliminating the spontaneous breathing of the patient again for a predetermined third period of time;
repeating steps (i)-(iii) until no ataxic breathing episode is detected any more during the second period of time.

According to a corresponding embodiment of the herein presented device, the controller is configured to
(i) control the pressure generator to discontinue the provision of the breathing gas after the predetermined period of time for at least a second predetermined period of time;
(ii) control the sensor to monitor the breathing pattern of the patient during the second predetermined period of time; and
(iii) control the pressure generator, if an ataxic breathing episode is detected during the second period of time, to provide again the flow of breathing gas for a predetermined third period of time with a volume per minute being above the individual-related threshold value of the patient so as to ventilate the patient and eliminate a spontaneous breathing of the patient;
wherein the controller is configured to repeat control steps (i)-(iii) until no ataxic breathing episode is detected any more during the second period of time.

This means, in other words, that after given amount of time the pressure support is reduced or turned off completely and the breathing of the patient is checked to see it the patient's autonomous breathing mechanism has stabilized. The breathing pattern of the patient is then monitored for a herein called second period of time.

If the breathing pattern continues or starts again to be irregular during this second period of time, the above-described re-synchronization therapy is repeated and the flow of breathing gas is provided for a predetermined third period of time. This third period of time may be equal to the above-mentioned first period of time. However, it may be also shorter or longer than the first period of time.

If, on the other hand, the breathing pattern stays regular while the breathing pattern of the patient is monitored during the second period of time, pressure support does not have to be picked up again until a new ataxic breathing episode is detected again. In this way a kind of a closed loop control is established.

According to a further embodiment of the presented method, each time step (iii) is repeated, the flow of breathing gas is provided with a volume per minute that is increased compared to the flow of breathing gas provided in a previous step (iii).

In a corresponding embodiment of the presented device, each time control step (iii) is repeated by the controller, the controller controls the pressure generator to provide the flow of breathing gas with a volume per minute that is increased compared to the flow of breathing gas provided in a previous control step (iii).

The reasoning behind this embodiment is the following: If after the first re-synchronization of the breathing pattern ataxic breathing episodes still occur, then, the next time the volume per minute will be increased in order to increase the likelihood of eliminating the ataxic breathing episodes. Increasing the volume per minute may be achieved either by increasing the flow rate or by increasing the time period of providing the gas flow.

The above-mentioned individual-related threshold value of the patient, which preferably equals the minute ventilation of the patient during regular breathing, may be determined in several ways.

According to an embodiment of the presented method, the individual-related threshold value of the patient may be determined by determining a minute ventilation of the patient when no ataxic breathing episode is detected in the monitored breathing pattern during sleep.

In the corresponding embodiment of the presented device, the controller is configured to determine the individual-related threshold value of the patient by determining a minute ventilation of the patient based on the breathing signal when no ataxic breathing episode is detected in the breathing pattern.

The generated flow of breathing gas that is delivered to the patient for re-synchronizing the breathing pattern may e.g. be set to be 20%, 30%, or even 50% above the determined individual-related threshold value (minute ventilation during regular breathing).

A still further possibility is to set the volume per minute of the generated flow of breathable gas to a fixed value of e.g. 6 l/m, since this value is for most patients above the "regular" minute ventilation and thus eliminates spontaneous breathing in almost all patients. However, such a pre-determining of the provided volume per minute is less preferable, if only because need for ventilation differs from patient to patient, as explained above.

A further possibility of determining the volume flow per minute that is required from eliminating the spontaneous breathing and re-synchronizing the breathing pattern may be the following: In an embodiment of the presented method, the step of ventilating the patient and eliminating the spontaneous breathing of the patient for the first period of time includes sensing one or more breathing parameters of the patient and increasing the volume per minute of the provided flow of breathing gas until the one or more sensed breathing parameters are synchronized with the provided flow of breathing gas, and then further increasing the volume per minute of the provided flow of breathing gas at this point by a predetermined fixed or relative extra value.

BRIEF DESCRIPTION OF THE DRAWINGS

These and other aspects of the invention will be apparent from and elucidated with reference to the embodiments described hereinafter. In the following drawings FIG. 1 schematically illustrates a respiratory therapy device according to an embodiment of the present invention.

DETAILED DESCRIPTION EXEMPLARY EMBODIMENTS

As used herein, the singular form of "a", "an", and "the" include plural references unless the context clearly dictates otherwise. As used herein, the terms "first", "second" merely distinguish between different components, time periods or features of the same type, but shall not imply any chronological order or a certain amount.

Directional phrases used herein, such as, for example and without limitation, top, bottom, left, right, upper, lower, front, back, and derivatives thereof, relate to the orientation of the elements shown in the drawings and are not limited upon the claims unless expressly recited therein.

The embodiments explained in the following are to be merely understood as exemplary embodiments of the herein presented device and method. These embodiments are described for the purpose of illustration based on what is currently considered to be most practical and preferred. However, on the contrary, it is intended to cover modifications and equivalent arrangements that are within the spirit and scope of the appended claims.

Figure 1:
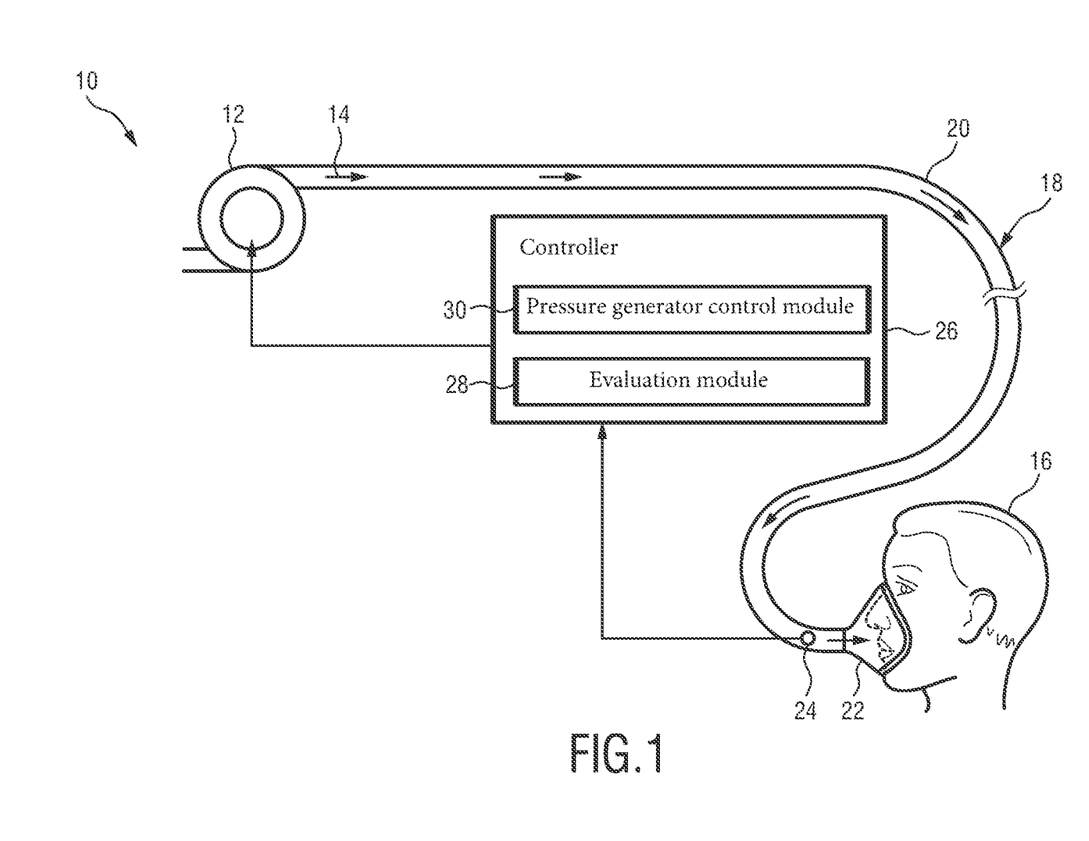

FIG. 1 schematically illustrates an exemplary embodiment of the respiratory therapy device according to the present invention. The device is therein in its entirety denoted by reference numeral 10.

The respiratory therapy device 10 comprises a gas flow generator 12 (also denoted as pressure generator 12) which is configured to generate a flow of breathing gas. Said generated flow of breathing gas is schematically indicated by arrows 14. The breathing gas may include air, oxygen, or a mixture thereof. It is delivered from the gas flow generator 12 to an airway of a patient 16 via a pressure circuit 18.

The pressure circuit 18 connects the pressure generator 12 to the airway of the patient 16. It may include a conduit or hose 20 which is connected at its a first end to the pressure generator 12 and at its second opposite end to a patient interface 22. The patient interface 22 is preferably configured to direct the generated flow of breathing gas 14 to the airway of the patient 16 in a non-invasive manner. The patient interface 22 may include a mask, such as a full face mask for covering the nose and mouth, a mouth mask for covering the mouth, a nose mask for covering the nose, or a total face mask for covering most parts of the face including the nose, the mouth and the eyes.

The pressure support system shown in FIG. 1 is what is usually known as a single-limb system, meaning that the pressure circuit 18 includes only one delivery conduit 20 connecting the patient 16 to the pressure generator 12.

The present invention also contemplates that the pressure support system can be a two-limb system, having a delivery conduit and an exhaust conduit connected to the patient 16. In a two-limb system, the exhaust conduit carries exhaust gas from the patient 16 and includes an exhaust valve at the end distal from the patient 16.

The pressure therapy device 10 furthermore comprises a sensor 24 and a controller 26. The sensor 24 is used for monitoring the breathing pattern of the patient 16. It generates a breathing signal that is indicative of the breathing pattern of the patient 16. The sensor 24 may include one or more sensors. The sensor 24 may e.g. comprise a flow sensor, a pressure sensor or an electrochemical gas sensor, and may be arranged at or within the patient interface 22 or within the delivery conduit 20 at a position close to the patient interface 22. In an alternative embodiment, the sensor 24 may include a camera or radar sensor that is arranged remote from the patient 16, the pressure generator 12, and the pressure circuit 18. This camera may monitor the movements of the patient's chest in order to derive the breathing signal. In a still further embodiment a radar sensor may be used for monitoring the chest movements of the patient 16 and thereby deriving the breathing signal.

The controller 26 is configured to control the pressure generator 12 based on a predefined operating algorithm and based on the breathing signal provided by the sensor 24. The controller 26 may include one or more of a digital processor, an analog processor, a digital circuit designed to process information, an analog circuit designed to process information, a state machine and/or other mechanisms for electronically processing information. Preferably, the controller 26 includes a CPU having software stored thereon for carrying out the mechanisms as explained below and for controlling the pressure generator 12 in the way explained below. Although controller 26 is shown in FIG. 1 as a single entity, this is for illustrative purposes only. In some implementations, controller 26 may include a plurality of processing units. These processing units may be physically located within the same device, or controller 26 may represent processing functionality of a plurality of devices operating in coordination.

The controller 26 may be configured to execute one or more computer program modules which are hardware and/or software implemented. The one or more computer program modules may include an evaluation module 28 and a pressure generator control module 30.

The evaluation module 28 is preferably configured to evaluate the breathing signal provided by the sensor 24 in order to detect whether the monitored breathing pattern of the patient 16 includes an ataxic breathing episode.

The pressure generator control module 30 is preferably configured to control the pressure generator 12 based on the evaluation of the breathing signal provided by the evaluation module 28. According to a preferred embodiment, the pressure generator control module 30 is configured to turn on the pressure generator 12 for providing the pressurized flow of breathing gas 14 only if the evaluation module 28 detects an ataxic breathing episode in the breathing signal provided by the sensor 24. In this case the pressure generator control module 30 preferably controls the pressure generator to provide the flow of breathing gas 14 for a predetermined period of time (herein denoted as first time period) with a volume per minute which is above an individual-related threshold value of the patient 16, wherein said individual-related threshold value corresponds or equals the minute ventilation of the patient 16 during regular breathing when no ataxic breathing occurs.

The pressure generator 12 is in other words controlled to provide a pressurized flow of breathing gas 14 that exceeds the "regular" minute ventilation of the patient 16. The provision of a pressurized flow of breathable gas 14 that exceeds the "normal" minute ventilation of the patient 16 results in an elimination of the spontaneous breathing of the patient 16 such that the patient 16 is completely mechanically ventilated by means of the pressure generator 12.

The elimination of the spontaneous breathing of the patient 16 overrides the person's irregular breathing pattern that occurs during ataxic breathing. This shall help to restore the balance between $O_2$ and $CO_2$, which balance is usually disordered during ataxic breathing, back to normal values again. The breathing pattern is thereby re-synchronized in similar way as a hearth rhythm is synchronized by an ICD.

Figure 2:
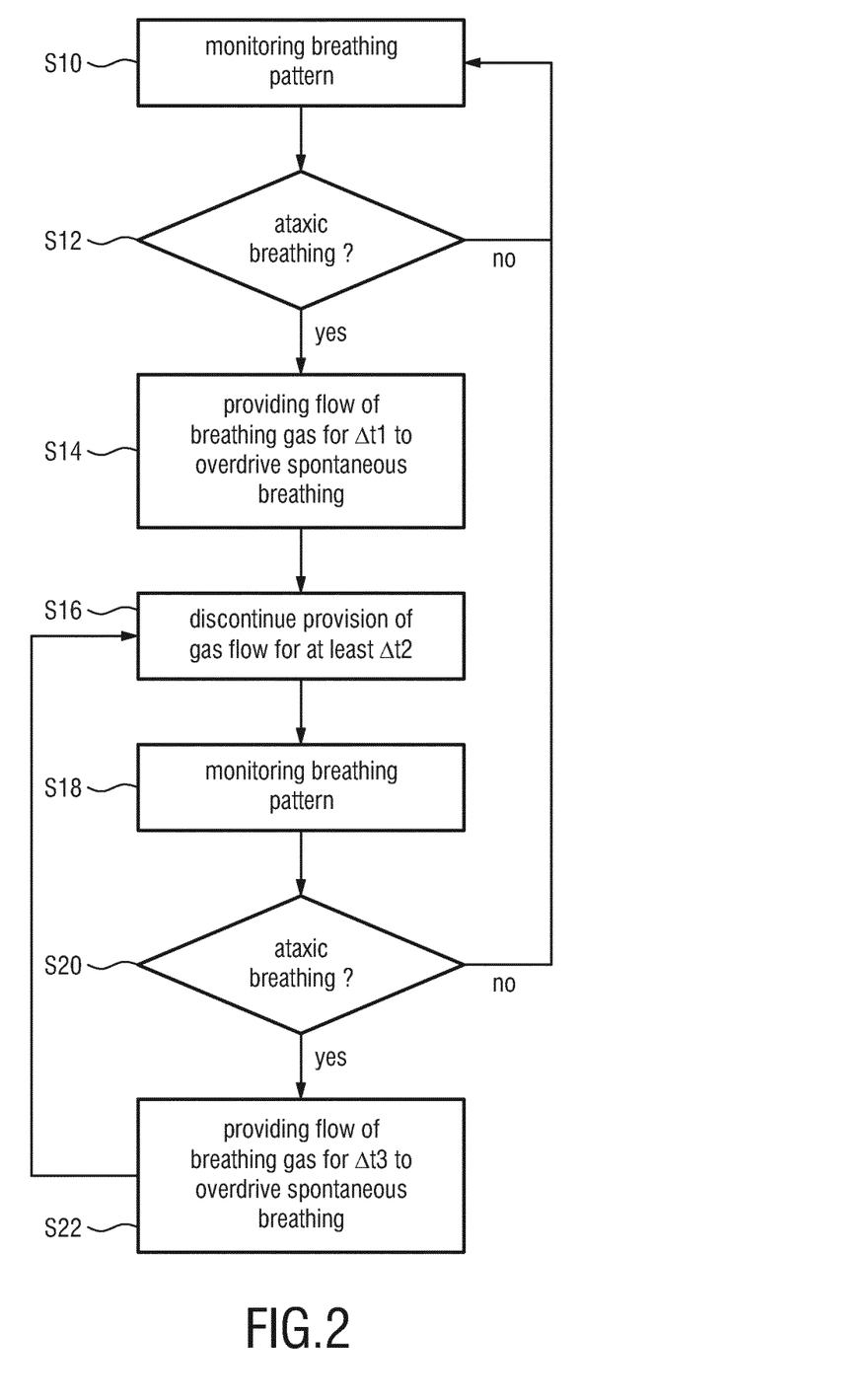
FIG. 2 illustrates an embodiment of a respiratory therapy method according to the present invention in form of a block diagram.

FIG. 1 shows a block diagram which schematically illustrates an embodiment of a method for re-synchronizing the breathing pattern of the patient 16. In a first step S10, the breathing pattern of the patient 16 is monitored, e.g. based on the breathing signal provided by the sensor 24. As long as no ataxic breathing episode occurs, the pressurized flow of breathable gas 14 may either be completely turned off or kept at a comparatively low level that allows the patient 16 to breathe spontaneously. This situation may, for example, be the case during time period 32 that is schematically illustrated in the volume flow-over-time graph shown in FIG. 3.

The breathing signal provided by sensor 24 may e.g. be sampled in regular intervals in order to detect whether the monitored breathing pattern includes an ataxic breathing episode (see step S12). As long as no ataxic breathing episode is detected in the monitored breathing pattern the method remains in a closed loop between step S10 and step S12.

If, on the other hand, an ataxic breathing episode is detected in the breathing signal, the afore-mentioned flow of breathing gas 14 is provided for a predetermined first time period $\Delta t_1$ to overdrive the spontaneous breathing of the patient 16 (see step S14).

Figure 3:
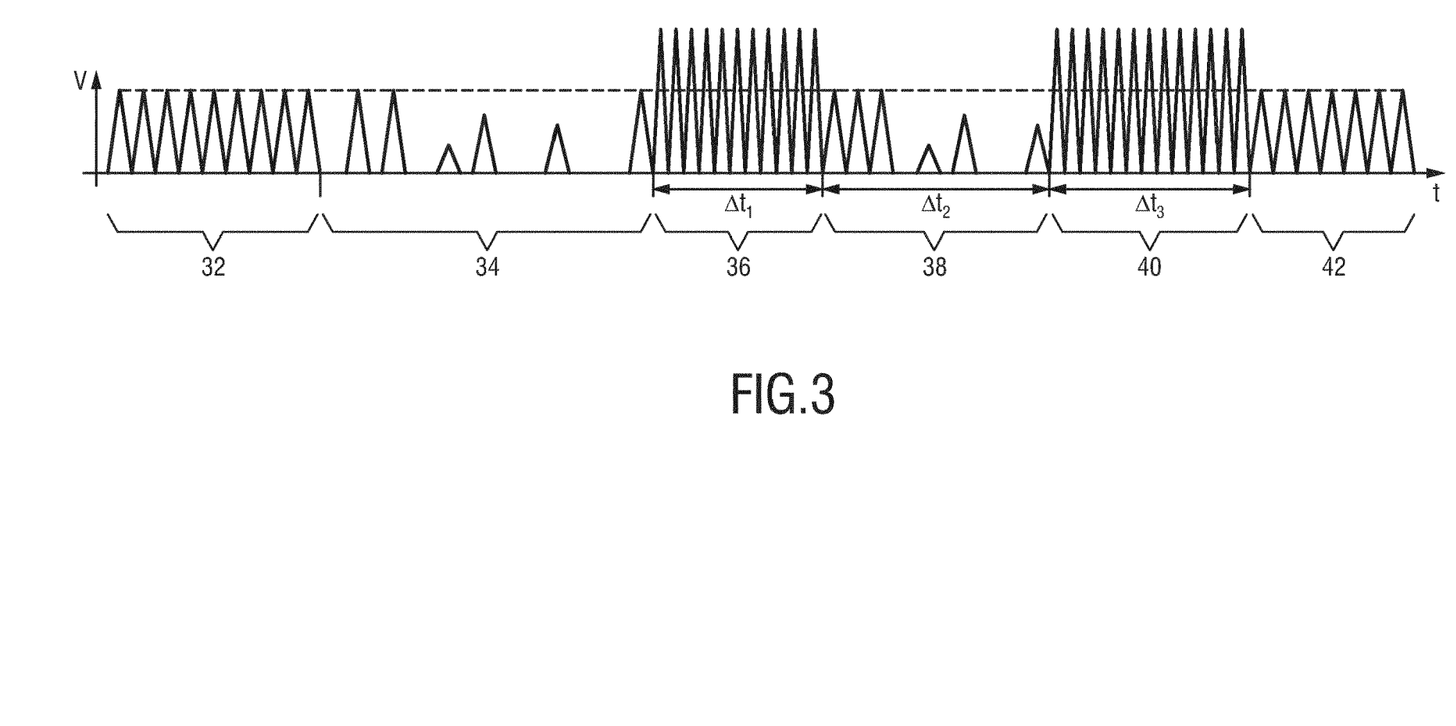
FIG. 3 shows a schematic graph that illustrates an exemplary volume flow over time of a breathing pattern of a patient.

A typical volume flow during ataxic breathing is depicted in FIG. 3 in time period 34. It may be seen that during this ataxic breathing time period 34 the amplitude, the frequency, and/or the minute ventilation vary rather strongly compared to regular breathing. It is therefore preferred to identify a part of the monitored breathing pattern of the patient 16 as ataxic breathing episode if a variation over time of one or more of the minute ventilation, the breathing frequency, and the breathing amplitude of the patient 16 is larger than a predetermined threshold. The minute ventilation, the breathing frequency, and/or the breathing amplitude are preferably derived from the breathing signal generated by the sensor 24.

The provision of the gas flow 14 for overdriving spontaneous breathing of the patient 16 during the first time period $\Delta t_1$ is schematically illustrated in time span 36 in FIG. 3. It can be seen that during this time period the volume per minute of the provided breathing gas flow 14 is above the minute ventilation during regular breathing (compare to time period 32 in FIG. 3).

The value for the minute ventilation that is to be set during the first time period $\Delta t_1$ may be determined in several ways:

One possibility is to determine the minute ventilation of the patient 16 when no ataxic breathing episode is detected in the monitored breathing pattern, e.g. during time period 32, and then to set the volume per minute of the provided gas flow 14 to a value above the determined "normal" minute ventilation (e.g. 10%, 20% or 50% above).

The second possibility is to use the breathing signal of the sensor 24 while the pressurized flow of breathing gas 14 is slowly ramped up. As long as the patient 16 is breathing spontaneously, the gas flow sensed by a flow sensor 24 will be influenced by the breathing effort of the patient 16. The flow of breathing gas 14 provided by the pressure generator 12 may thus be slowly ramped up until the sensed breathing parameters (e.g. the sensed inhaled and exhaled breathing flow of the patient 16) is synchronized with the flow of breathing gas 14 provided by the pressure generator 12. At this point mechanical ventilation of the patient 16 begins and spontaneous breathing is eliminated. If this point is detected, the controller 26 may control the pressure generator 12 to further increase the volume per minute of the provided flow of breathing gas 14 by an additional predetermined fixed or relative extra value.

It shall be noted that independent of the way how the volume per minute of the gas flow 14 is determined and set, spontaneous breathing is overdriven only for the predetermined first period of time $\Delta t_1$. This first time period $\Delta t_1$ may be equal to or less than one minute, equal to or less than two minutes, or equal to or less than five minutes. After that time period $\Delta t_1$ the flow of gas 14 is preferably turned off or reduced to a level below the regular minute ventilation of the patient 16. Time period 38 schematically illustrated in FIG. 3 shows a corresponding situation. This situation corresponds to method step S16 during which the provision of the gas flow 14 is discontinued/interrupted for at least a second period of time $\Delta t_2$. The breathing pattern of the patient 16 is monitored again by the sensor 24 during the second time period $\Delta t_2$ (see step S18).

If no ataxic breathing episode occurs during time period $\Delta t_2$, the method may return to step S10 (see method step S20).

If, however, an ataxic breathing episode is detected again during time period $\Delta t_2$, the pressure generator 12 may be controlled to again provide the breathing gas flow 14 to overdrive spontaneous breathing of the patient 16 (see step S22). The method may afterwards return to step S16 so as to repeat method steps S16-S22 until no ataxic breathing episodes are detected anymore (see FIG. 2).

In the example shown in FIG. 3 the breathing pattern of the patient 16 at first sight returns to a normal state after the first provision of the gas flow 14 during time period 36 (see beginning of time period 38 in FIG. 3). However, then ataxic breathing begins again. This could be e.g. the case if the re-synchronization provided during time period 36 has not been enough to completely eliminate ataxic breathing. The gas flow 14 is therefore provided again during time period 40 in the example shown in FIG. 3. The controller 26 of the device 10 may be configured to control the pressure generator 12 to provide the flow of breathing gas this time for a third time period $\Delta t_3$ which is longer than the first time period $\Delta t_1$. This shall increase the likelihood of eliminating the occurrence of an ataxic breathing episode. Alternatively, the same effect may be achieved if the third time period $\Delta t_3$ equals the first time period $\Delta t_1$ and the flow rate during the third time period $\Delta t_3$ is increased compared to the flow rate applied during the first time period $\Delta t_1$. According to an another embodiment, the third time period $\Delta t_3$ may even be or shorter than the first time period $\Delta t_1$.

It may be also seen in the example schematically illustrated in FIG. 3 that the breathing of the patient 16 returns to a normal state without any occurrence of an ataxic breathing episode in time period 42 after the second re-synchronization of the breathing pattern (during time period 40).

Lastly, it shall be noted that the provided flow of breathing gas 14 is preferably designed to be an oscillating gas flow. This may include a sinusoidal behavior of the volume flow but may also include indiscrete changes between phases of high level pressure (during inhalation) and phases of low level pressure (during exhalation).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Method for re-synchronizing a breathing pattern of a patient suffering from ataxic breathing, the method including the steps of:
   monitoring the breathing pattern of the patient during sleep;
   detecting that the monitored breathing pattern includes an ataxic breathing episode; and
   in response to detecting that the monitored breathing pattern includes the ataxic breathing episode, ventilating the patient and eliminating a spontaneous breathing of the patient for a predetermined first period of time ($\Delta t_1$) by providing a flow of breathing gas to an airway of the patient with a volume of the breathing gas provided per minute being above an individual-related threshold value of the patient.

2. The method according to claim 1, wherein detecting the ataxic breathing episode includes evaluating one or more of a minute ventilation, a breathing frequency, and a breathing amplitude of the patient.

3. The method according to claim 2, wherein a part of the monitored breathing pattern of the patient is identified the ataxic breathing episode if a variation over time of the one or more of the minute ventilation, the breathing frequency, and the breathing amplitude of the patient is larger than a predetermined threshold.

4. The method according to claim 1, further comprising the steps of:
   discontinuing the flow of the breathing gas after the predetermined period of time for at least a second predetermined period of time($\Delta t_2$);
   (ii) monitoring the breathing pattern of the patient during the second predetermined period of time ($\Delta t_2$);
   (iii) if another ataxic breathing episode is detected during the second period of time ($\Delta t_2$), ventilating the patient and eliminating the spontaneous breathing of the patient again for a predetermined third period of time ($\Delta t_3$);
   repeating steps (i)-(iii) until no ataxic breathing episode is detected any more during the second period of time ($\Delta t_2$).

5. The method according to claim 4, wherein each time step (iii) is repeated, the flow of breathing gas is provided with a volume per minute that is increased compared to the flow of breathing gas provided in a previous step (iii).

6. The method according to claim 1, further comprising the step of determining the individual-related threshold value of the patient by determining a minute ventilation of the patient when no ataxic breathing episode is detected in the monitored breathing pattern.

7. The method according to claim 1, wherein the step of ventilating the patient and eliminating the spontaneous breathing of the patient for the first period of time ($\Delta t_1$) includes sensing one or more breathing parameters of the patient and increasing the volume per minute of the provided flow of breathing gas until the one or more sensed breathing parameters are synchronized with the provided flow of breathing gas, and then further increasing the volume per minute of the provided flow of breathing gas at this point by a predetermined fixed or relative extra value.

8. The method according to claim 1, wherein the provided flow of breathing gas is an oscillating gas flow.

9. A device for re-synchronizing a breathing pattern of a patient suffering from ataxic breathing, comprising:
   a sensor for monitoring the breathing pattern of the patient during sleep, wherein the sensor generates a breathing signal;
   a pressure generator for generating a flow of breathing gas;
   a pressure circuit including a patient interface for guiding the generated flow of breathing gas to an airway of the patient; and
   a controller which is configured to:
      evaluate the breathing signal in order to detect whether the monitored breathing pattern includes an ataxic breathing episode; and
      if the ataxic breathing episode is detected in the breathing signal, control the pressure generator to provide for a predetermined first period of time ($\Delta t_1$) the flow of breathing gas with a volume per minute being above an individual-related threshold value of the patient so as to ventilate the patient and eliminate a spontaneous breathing of the patient for said predetermined first period of time ($\Delta t_1$).

10. The device according to claim 9, wherein the sensor includes at least one of a flow sensor, a pressure sensor, a camera, a radar sensor, an accelerometer, a piezoelectric sensor and an electrochemical gas sensor.

11. The device according to claim 9, wherein the controller is configured to:
    determine one or more of a minute ventilation, a breathing frequency, and a breathing amplitude of the patient based on the breathing signal;
    evaluate a variation over time of the one or more of the minute ventilation, the breathing frequency, and the breathing amplitude; and
    identify a part of the monitored breathing pattern of the patient as ataxic breathing episode if the variation over time of the one or more of the minute ventilation, the breathing frequency, and the breathing amplitude of the patient is larger than a predetermined threshold.

12. The device according to claim 9, wherein the controller is configured to:
    control the pressure generator to discontinue the flow of the breathing gas after the predetermined period of time for at least a second predetermined period of time ($\Delta t_2$);
    (ii) control the sensor to monitor the breathing pattern of the patient during the second predetermined period of time ($\Delta t_2$); and
    (iii) control the pressure generator, if another ataxic breathing episode is detected during the second period of time ($\Delta t_2$), to provide again the flow of breathing gas for a predetermined third period of time (($\Delta t_3$) with the volume per minute being above the individual-related threshold value of the patient so as to ventilate the patient and eliminate the spontaneous breathing of the patient;
    wherein the controller is configured to repeat control steps (i)-(iii) until no ataxic breathing episode is detected any more during the second period of time ($\Delta t_2$).

13. The device according to claim 12, wherein each time control step (iii) is repeated by the controller, the controller controls the pressure generator to provide the flow of breathing gas with the volume per minute that is increased compared to the flow of breathing gas provided in a previous control step (iii).

14. The device according to claim 9, wherein the controller is configured to determine the individual-related threshold value of the patient by determining a minute ventilation of the patient based on the breathing signal when no ataxic breathing episode is detected in the monitored breathing pattern.

* * * * *